United States Patent [19]

Hamilton

[11] Patent Number: 4,796,790
[45] Date of Patent: Jan. 10, 1989

[54] MEDICAL SUPPLY CASE

[76] Inventor: Olivia B. Hamilton, 5120 Sargent Rd., NE., Apt. 207, Washington, D.C. 20017

[21] Appl. No.: 917,204

[22] Filed: Oct. 9, 1986

[51] Int. Cl.$^4$ .............................................. A45F 5/00
[52] U.S. Cl. .................... 224/253; 224/227; 224/228; 224/241; 224/250; 206/828; 206/570; 206/438; 206/803
[58] Field of Search ............... 206/570, 569, 438, 803, 206/828; 224/237, 228, 196, 197, 241, 250, 252, 240, 253, 236, 226, 227

[56] References Cited

U.S. PATENT DOCUMENTS

| | | | |
|---|---|---|---|
| 668,466 | 2/1901 | Taylor et al. | |
| 750,465 | 1/1904 | Koch | 206/570 X |
| 967,487 | 8/1910 | Baker | 224/197 |
| 1,558,213 | 10/1925 | Atkins | 224/196 |
| 2,764,327 | 9/1956 | Stevenson | 224/236 X |
| 2,804,969 | 9/1957 | Barnett | 206/570 X |
| 3,096,010 | 7/1963 | Rasmussen | 224/250 |
| 3,185,362 | 5/1965 | Wakefield | 224/155 |
| 3,212,690 | 10/1965 | Green | 224/151 |
| 3,361,312 | 1/1968 | Hutchison | 224/240 |
| 3,389,784 | 6/1968 | Hendricks et al. | 206/803 X |
| 3,552,610 | 1/1971 | Coleman et al. | 224/240 |
| 3,949,916 | 4/1976 | Yount | 224/240 |
| 4,047,650 | 9/1977 | Domingos | 224/236 X |
| 4,084,734 | 4/1978 | Bianchi et al. | 224/206 X |
| 4,236,657 | 12/1980 | Brunton | 224/237 X |
| 4,441,639 | 4/1984 | Craw et al. | 224/237 |
| 4,513,866 | 4/1985 | Thomas | 206/570 |

OTHER PUBLICATIONS

Reeves Pocket Packet, (date unknown).
The Pac.Kit, (date unknown).
Uniform Accessories-Nylon Pocket Organizer, (date unknown).

Primary Examiner—Henry J. Recla
Attorney, Agent, or Firm—Banner, Birch, McKie & Beckett

[57] ABSTRACT

A medical supply case for organizing and holding various small medical supplies and to be worn and/or carried by medical personnel. A first panel is provided having a first panel front side, a first panel rear side, and a front side supply pocket. A second panel is connected to the first panel and has a second panel front side, and a second panel rear side, a rear side supply pocket. A hinge connects the sides of the first and second panels for positioning the first and second panels relative to each other in a first position wherein the first panel front side is generally adjacent and facing the second panel front side and alternately in a second position wherein the second panel rear side is generally adjacent and facing the first panel rear side. A first securing device releasably secures the first and second panels in the first position, and a second securing device releasably secures the first and second panels in the second position. This arrangement allows the user to have the pockets containing the articles needed for the task at hand to be accessibly positioned, preferably in front when worn by the user. A flap is connected to the first panel and is movable to alternative positions disposed between the first and second panels, or positioned generally adjacent the second panel rear side. A user belt is connected to the first panel so that the first and second panels can be held from the user's waist or shoulder. When the flap is secured across the face of the panels the medical supply case can be removed from the belt with its contents well secured inside and the case then placed in the user's lab coat pocket.

52 Claims, 3 Drawing Sheets

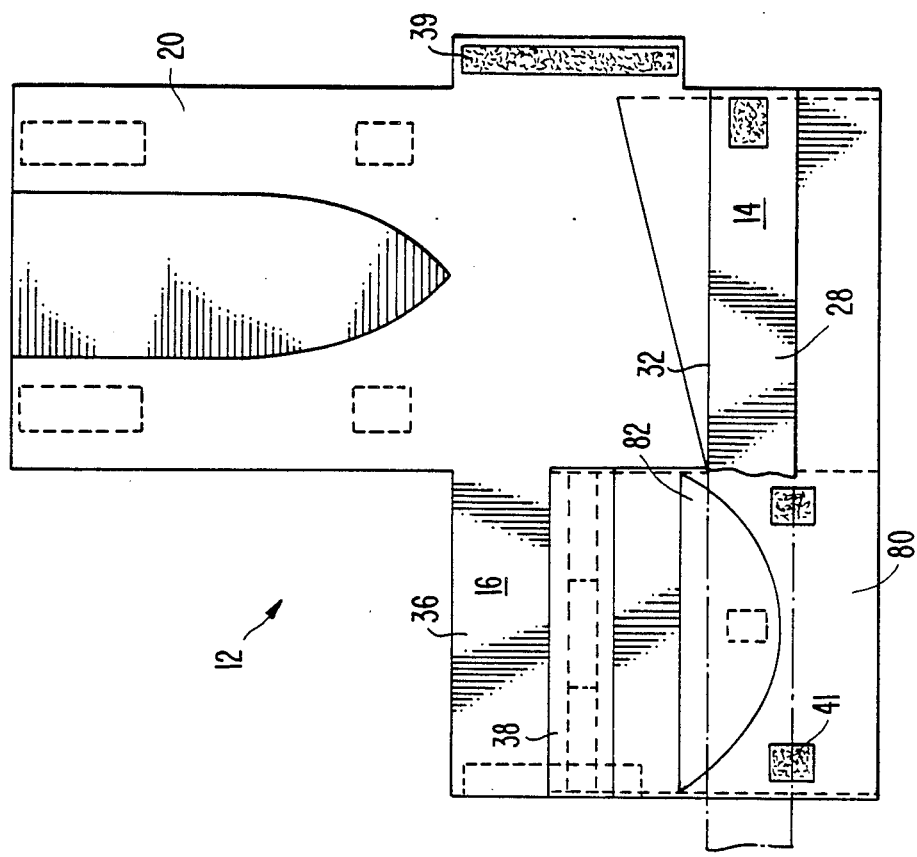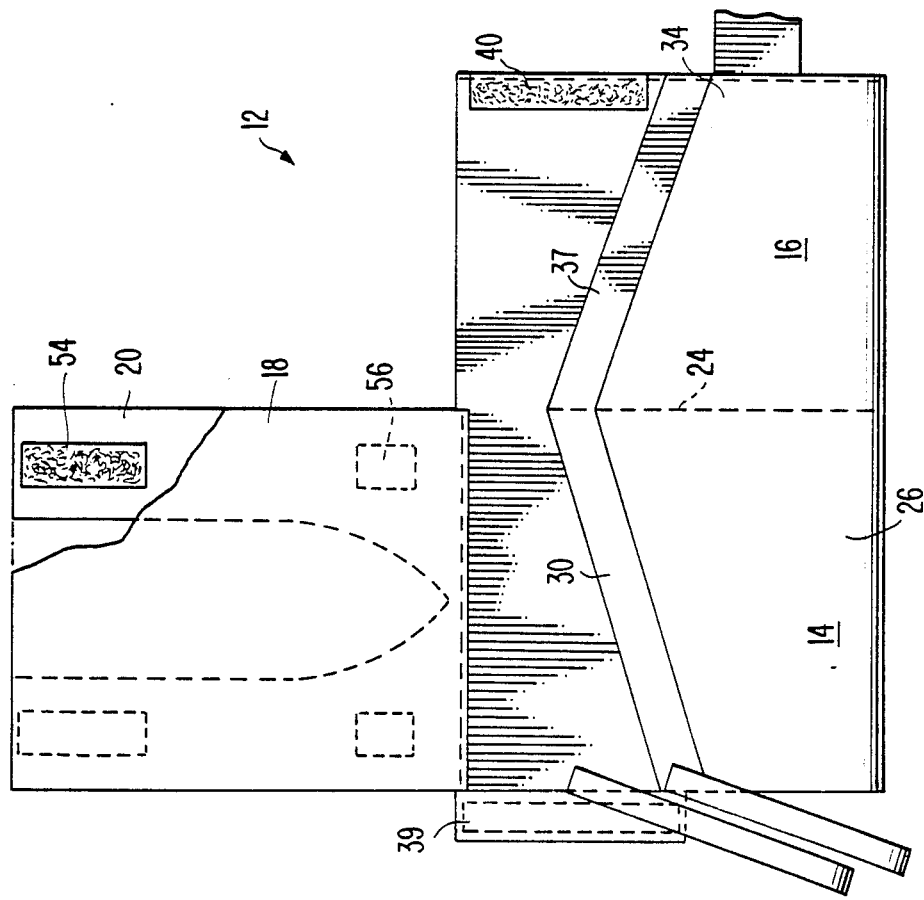

MEDICAL SUPPLY CASE

BACKGROUND OF THE INVENTION

The present invention relates to packets or cases for organizing and holding small medical supplies. These cases are used and worn by medical personnel such as nurses, nurse's assistants, student nurses, medical students, interns, and residents.

Many small packets or kits are known for organizing and holding small medical supplies. Examples of such kits are those marketed under the names of "Reeves Pocket-Packet", "Uniform Accessories Nylon Packet Organizer", "The Pac-Kit", and "Flexiflo". Generally, these kits are formed simply by a panel of material with one or more pockets, key clips, fastened coin pockets, and/or belt loops. Another similar example is that shown in U. S. Pat. No. 668,466, the contents of which are hereby incorporated by reference in their entirety.

The currently available packets or cases are inadequate though for the needs of today's medical personnel. They do not accommodate enough medical supplies nor do they position them so that they are readily accessible by the personnel. They have limited carrying capacity so that the medical personnel must return frequently to their supply stations to pick up additional supplies. This interrupts the medical procedure and makes it less efficient and more costly. It also encourages the medical personnel to take unnecessary and possibly dangerous short cuts in their work when they do not have the necessary supplies with them. Medical supply cases known in the art further do not provide for an efficient means for securing the supplies within the case so that they do not become dirtied or fall out of the case. This is especially important when the personnel are on their breaks, and take the case with them, such as to the cafeterias. Further with the system of diagnostic related illnesses and the pressures on the hospitals to keep costs down, the workload has increased for the medical personnel, especially the nurses, who often are required to also do the work previously done by the nurse's aides. It is imperative that the medical personnel be as efficient as possible and do not lose time going back and forth to get the needed supplies.

OBJECTS OF THE INVENTION

Accordingly, it is a principal object of the present invention to provide an improved medical supply packet or case for organizing and holding small medical supplies and adapted to be worn by medical personnel.

Another object of the present invention is to provide an improved medical supply case having a greater number of pockets for organizing and containing greater number of small medical supplies.

A further object of the present invention is to provide an improved medical supply kit having greater carrying capacity and also designed to be folded into a compact packet which can easily be carried in lab coat pockets.

A still further object of the present invention is to provide an improved medical supply case which can be in a first mode exposing at least some of the pockets to the exterior for easy access by the personnel and a second mode wherein the articles are protected from the exterior and secured in the case.

Another object is to provide an improved medical supply case having greater numbers of pockets each of which can be easily and quickly accessed by the personnel when the medical supply case is secured to the personnel, as from his belt, without requiring that the case be first removed from the belt.

A further object is to provide an improved medical supply case which can carry and efficiently organize a variety of small medical articles of different sizes and shapes.

A still further object is to provide an improved medical supply case which allows the medical personnel to be more efficient in their various duties.

Other objects and advantages of the present invention will become more apparent to those persons having ordinary skill in the art to which the present invention pertains from the following description taken in conjunction with the accompanying drawings.

BRIEF DESCRIPTION OF THE DRAWINGS

FIG. 4 is a front elevational view of the supply case of FIG. 1 illustrated in its fully opened position as in FIG. 3.

FIG. 5 is a rear elevational view of the supply case of FIG. 1 shown in its fully opened position.

DETAILED DESCRIPTION OF THE PREFERRED EMBODIMENTS

Figure 1:
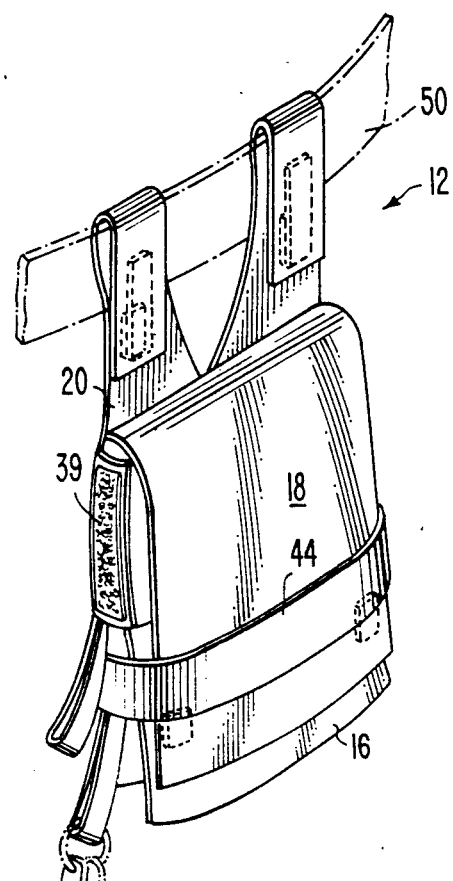
FIG. 1 is a front perspective view of a medical supply case of the present invention.
Figure 2:
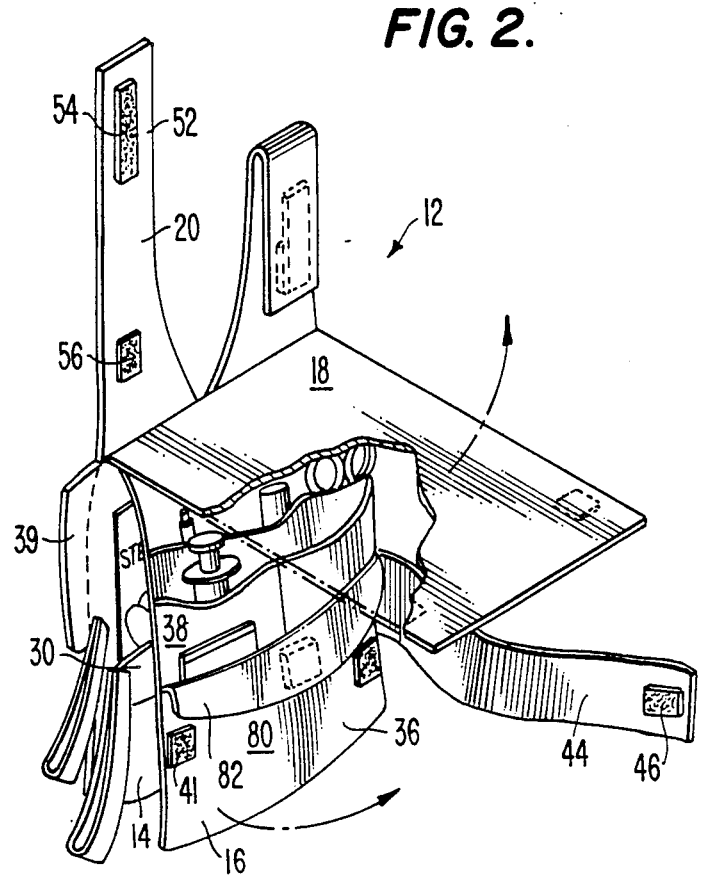
FIG. 2 is a view similar to FIG. 1 illustrating the supply case being opened, and having a portion of the top flap broken away for the sake of clarity.
Figure 3:
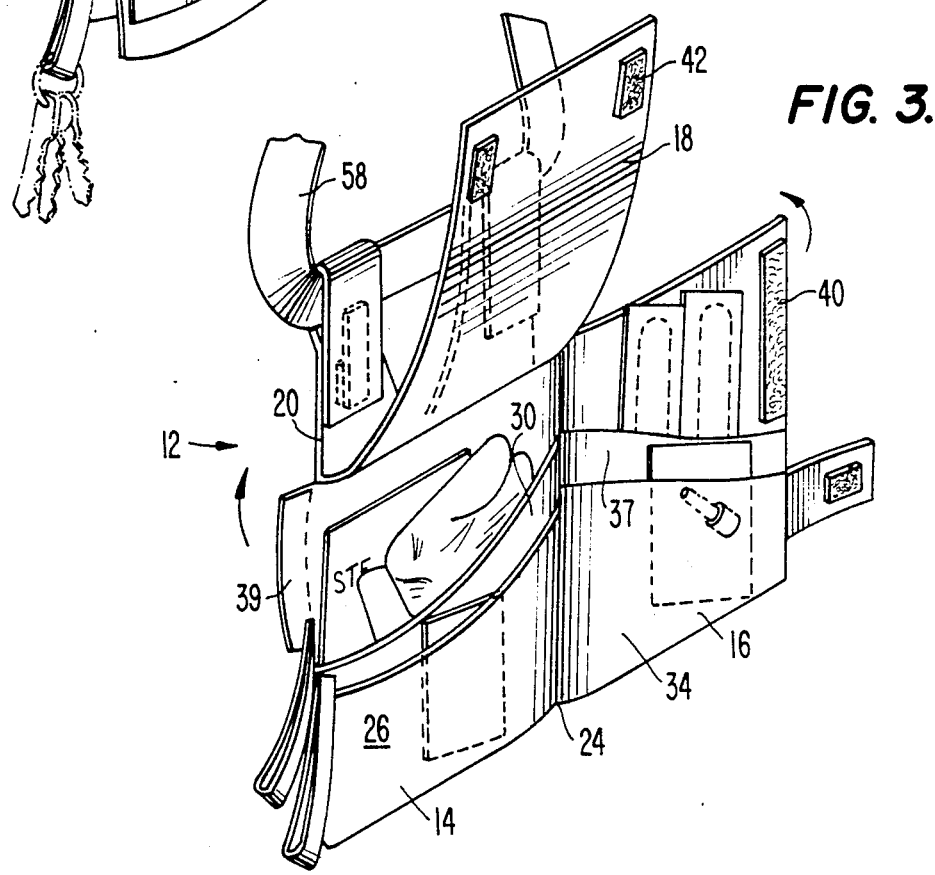
FIG. 3 is a view similar to FIGS. 1 and 2 illustrating the supply case in its fully opened position.

Referring to FIGS. 1-5, a first embodiment of the present invention is illustrated generally at 12. Supply case 12 is shown to comprise a first panel 14, a second panel 16, a top flap 18, and an attaching means 20 for attaching the first panel to the medical personnel. Second panel 16 is attached to first panel 14 along its side edge and is attached in a hinged fashion along hinge line 24 so that case 12 can open like a book to expose the interior pockets. First panel 14 has front and back sides 26, 28, each of which is provided with at least one pocket 30, 32, respectively. Second panel 16 similarly has a front side as shown in FIG. 3 at 34 and a back side as shown in FIG. 2 at 36, each provided with pockets 37, 38, respectively. First and second panels 14, 16 can be positioned in alternative first and second positions relative to one another. The first position is best illustrated in FIG. 2 which shows that the first panel front side 26 and the second panel front side 34 are positioned facing and adjacent each other. The VELCRO hook and loop type of fastener panel 39 secured to the upper left portion of first panel 14, and the VELCRO hook and loop type of fastener surface is on the back side thereof as viewed in FIGS. 2 and 3, is folded to the front side of the first panel and VELCRO hook and loop type of fastener panel 40 secured to the second panel front side 34 engages panel 39 to secure the first and second panels 14, 16 in the first position. VELCRO hook and loop type of fastener or hook and loop type fasteners, are disclosed herein at several places but any other type of suitable releasable fastening means, such as grippers or ties, is within the scope of this invention.

When in the first position top flap 18 can be positioned in one of two flap positions. In the first position top flap 18 is disposed or sandwiched between the first and second panels 14, 16. This allows second panel back side 36 to be exposed and its pocket's contents readily visible and accessible to the personnel. Alternatively, top flap 18 can be positioned outside of second panel 16 and secured to its back (or forward facing) side by VELCRO hook and loop type of fastener pads 41 on the second panel back side 36 as best shown in FIG. 2 and by VELCRO hook and loop type of fastener pads 42 on top flap 18 as shown in FIGS. 2 and 3. When in this position the panels and flap can be further secured together with the longitudinal belt 44 wrapping around the face of the second panel and fastened with a releasable VELCRO hook and loop type of fastener means as shown in FIG. 2 at 46 to first panel back side 28.

As mentioned above, the first and second panels 14, 16 can be placed in an alternative second position wherein second panel back side 36 is positioned adjacent first panel back side 28. This can be visualized, referring to FIG. 3, by further folding second panel 16 until it is behind first panel 14. The first panel VELCRO hook and loop type of fastener strip 39 is then folded rearward onto the second panel VELCRO hook and loop type of fastener strip, thereby exposing pockets 30 of the first panel front side and the articles contained in them to the medical personnel. As can be appreciated, this different positioning, i.e., the first and second positions of the panels, allows the medical personnel to very easily expose the different items needed at the various times for convenient access.

It further is noted that supply case 12 can be readily repositioned to expose the needed articles while the case is secured to the personnel. The case can be secured by any suitable means 20, including around his waist or over his shoulder. For attachment to the waist a belt 50 can be provided with the case. Alternatively, belt loops 52 can be included to attach to the personnel's existing belt. This can be by means of mating VELCRO hook and loop type of fastener attachment on the loops as illustrated in FIG. 2 at 54, 56. A similar type of VELCRO hook and loop type of fastener loop attachment can be used for attaching it to a shoulder harness or strap as shown in FIG. 3 at 58.

Figure 6:
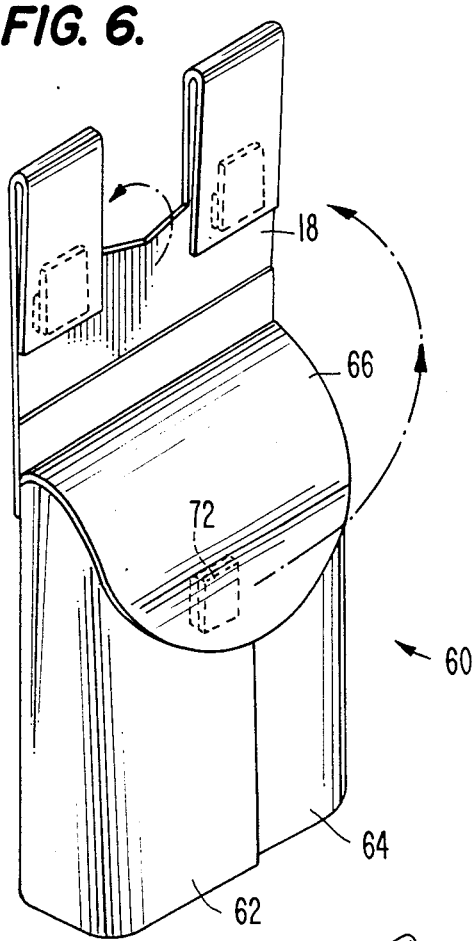
FIG. 6 is a front perspective view of a second embodiment of the present invention illustrated in its closed condition.

A second embodiment of the present invention is illustrated generally at 60 in FIGS. 6-9. Referring thereto, it is seen that supply case 60 similarly includes the first and second panels 14, 16 wherein second panel 16 folds like a book relative the first panel 16 between a first position adjacent the front of the first panel and a second position adjacent the back side of the first panel. Instead of providing a top flap which is generally the same size and shape as the panels (as is top flap 18), a series of three flaps is provided. This series includes two side flaps 62, 64 attached to opposite sides of first panel 14 and a smaller front top flap 66 attached along the upper edge of first panel 14. When the first and second panels are in the first position, that is, when their front sides are adjacent one another, the left and right side flaps 62, 64 can be positioned on the rear side of the front panel (as illustrated by the arrows in FIG. 7) and secured thereto by VELCRO hook and loop type of fastener strips. Top flap 66 then can be positioned between the first and second panels. When in this panel and flap position the rear side of the second panel is outwardly exposed and its pockets, and the contents thereof, are readily visible and accessible. Also, when the first and second panels are in the first position the flaps can be secured to the outside, or the rear, of the second panel as illustrated in FIG. 6. When in this position, left and right flaps 62, 64 are held to each other by VELCRO hook and loop type of fastener strips and top flap 66 is folded on top of them and similarly secured thereto by strip 72. When the first and second panels are in the second position the left side flap can be positioned either on the front or rear side of the first panel.

Figure 7:
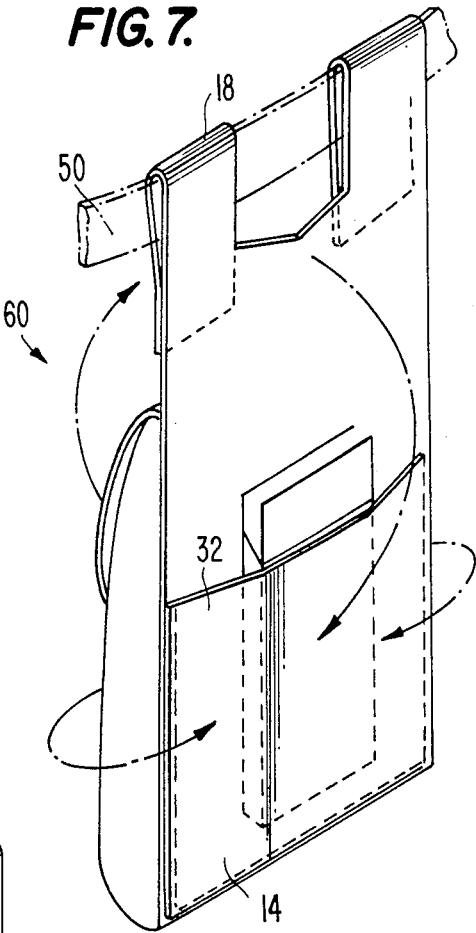
FIG. 7 is a rear perspective view of the medical supply case of FIG. 6 illustrated in its closed position; the arrows therein illustrate the overfolding of the side and top flaps.
Figure 8:
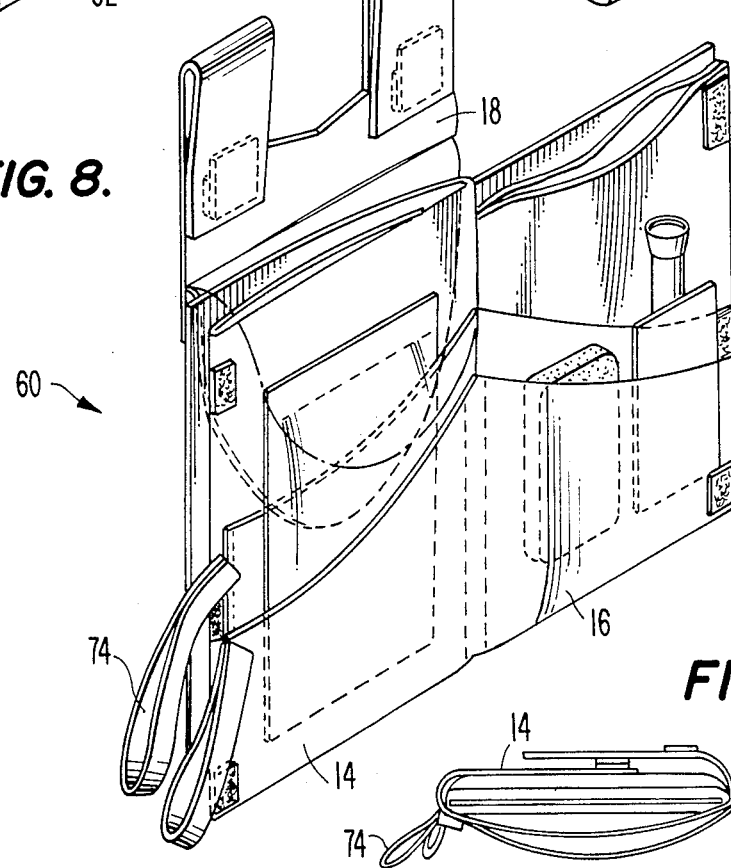
FIG. 8 is a fragmentary front perspective view of the case of FIG. 6 illustrated in its fully opened position.
Figure 9:
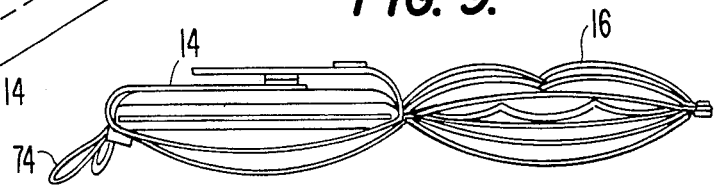
FIG. 9 is a top plan view of the case of FIG. 8 illustrating each of the pockets.

In addition to the pockets, suitable loops 74 to which keys can be fastened are provided, and are configured and placed so that the keys when attached to the loops can be inserted between the positioned first and second panels and held therein or positioned outside of the case as shown in FIG. 1. The pockets can be of various shapes and sizes to hold a variety of different articles. Referring to FIGS. 3 and 4, the pockets can be overlapping and staggered so that the articles in the forward and rear overlapping pockets are simultaneously visible and accessible. The pockets can also be formed as by vertical stitching to define a plurality of side-by-side vertical pockets for separately holding elongated articles, such as pens and pencils. The pocket on the rear side of the first panel, as shown in FIG. 7, is perhaps best suited for flat articles such as a notepad or a package of cigarettes so that supply case 12 can rest smoothly against the wearer's front body side. Numerous articles can be held within the pockets and many are illustrated in the drawings. The articles which can be contained though are not to be limited to those illustrated nor to the exemplary list which follows. The articles can include alcohol prep pads, iodine prep pads, bandages, tongue depressors, magic markers, pens, pencils, hemostats, penlights, scissors, teagaderm, intermittent infusion plug, hepra-in-flush needles, gloves, syringes, gauze, sponges, tape, keys, lotion, comb, lubrfax, safety pins, external cuth, lemon swab sticks, and A and D. ointment. Further, they can include vaseline ointment, vacatainer butterflies, intercath, and so forth. Also, it is within the scope of the present invention to provide a change purse 80 with a downwardly closing flap 82 as shown in FIGS. 2 and 5. The environment, work requirements and personal needs of the user will help determine the articles to be carried.

As can be appreciated, the carrying capacities of supply cases 12 and 60 are great and yet the filled cases are not too large or bulky. They can be easily carried on a belt, in a pocket or by hand. Further, the hinged panel designs provides for alternative positioning of the panels as the medical personnel user makes his or her rounds so that a different pocket side and thus the articles carried in it are exposed for easy access at the different medical stations. Also, the securing flaps can be easily positioned to cover and secure the articles in the pockets, and later repositioning out of the way.

From the foregoing detailed description, it will be evident that there are a number of changes, adaptations, and modifications of the present invention which come within the province of those skilled in the art. However, it is intended that all such variations not departing from the spririt of the invention be considered as within the scope thereof as limited solely by the claims appended hereto.

What is claimed is:

1. A medical supply case for organizing and holding small medical supplies and to be worn or carried by medical personnel comprising:
 a first panel having a first panel front side, a first panel rear side, and a first panel side edge,
 a second panel connected to said first panel and having a second panel inside side, a second panel outside side, and a second panel side edge,
 a hinge means for positioning said first and second panels relative to each other alternatively in a first position wherein said first panel front side is generally facing said second panel inside side and a second position wherein said second panel outside side is generally facing said first panel rear side,
 a first securing means for releasably securing said first and second panels in said first position,
 a supply pocket on said first panel front side,
 a supply pocket on said second panel outside side,
 a flap connected generally to said first panel and movable to and between alternative first and second flap positions,
 said flap when in said first flap position being disposed between said first and second panels,
 said flap when in said second flap position being disposed outside of said second panel outside side,
 an attaching means for attaching said first panel to the medical personnel, and
 said hinge means being generally vertically disposed when said first panel is worn by the medical personnel by way of said attaching means.

2. The case of claim 1 including,
said first and second panels being in said first position when said flap is in said first flap position.

3. The case of claim 1 including,
said first and second panels being in said first position when said flap is in said second flap position.

4. The case of claim 1 including,
said first panel including a first panel upper edge, and
said flap being secured along said first panel upper edge.

5. The case of claim 1 including,
a flap securing means for releasably securing said flap to said second panel when in said second flap position.

6. The case of claim 1 including,
a securing belt extending across the face of said second panel outside side to said first panel rear side when said first and second panels are in said first position.

7. The case of claim 6 including,
a securing means for releasably securing one end of said securing belt to said first panel rear side.

8. The case of claim 7 including,
said securing belt including another end thereof which is attached to said hinge means.

9. The case of claim 1 including,
said attaching means comprising a connecting means for connecting said first panel to a belt of the medical personnel user of said case so that said first panel hangs therefrom.

10. The case of claim 1 including,
said attaching means comprising a user waist belt connected to said first panel.

11. The case of claim 1 including,
said attaching means comprising a user shoulder belt connected to said first panel.

12. The case of claim 1 including,
said supply pocket of said first panel front side being open at its top for inserting articles down into it.

13. The case of claim 1 including,
said supply pocket of said first panel front side comprising a first pocket defining a first compartment and a second pocket overlying said first pocket and defining a second compartment.

14. The case of claim 1 including,
said first and second panels being formed from a single continuous piece of material.

15. The case of claim 14 including,
said hinge means comprising stitching in said material between said first and second panels.

16. The case of claim 1 including,
said supply pocket of said front panel being defined on the first surface thereof by a pocket panel secured along three of its four sides to said front panel and on its rear surface by said front panel.

17. The case of claim 1 including,
a loop connected to said first panel through which keys can be removably attached, and positionable between said first and second panels when said first and second panels are in said first position.

18. The case of claim 17 including,
said loop and said supply pocket on said first panel front side being positioned so that keys when attached to said loop can be positioned in said supply pocket on said first panel front side.

19. The case of claim 1 including,
said pocket on said second panel rear side including a downwardly positionable pocket flap for covering the upper opening thereof, and a means for releasably securing said pocket flap in a closed position.

20. The case of claim 1 including,
said second panel being movable relative to said first panel and to said attaching means.

21. The case of claim 20 including,
said second panel being movable about said hinge means between said first and second positions when said attaching means is attaching said first panel to the medical personnel.

22. The case of claim 20 including,
said attaching means comprising a waist belt.

23. The case of claim 20 including,
said attaching means comprising a shoulder belt.

24. The case of claim 20 including,
said attaching means comprising a means for attaching said first panel so that it hangs from a belt of the medical personnel.

25. The case of claim 1 including,
a supply pocket on said first panel rear side.

26. The case of claim 1 including,
said first and second panels each being about five and one-half inches wide and six inches long.

27. The case of claim 1 including,
said first and second panels being formed of nylon pack cloth.

28. The case of claim 1 including,
a change purse attached to said second panel outside side.

29. The case of claim 1 including,
said first and second panels being formed of nylon.

30. The case of claim including,
a supply pocket on said second panel inside side.

31. The case of claim 1 including, a flap which covers said supply pocket on said second panel rear side when said first and second panels are in said first position.

32. The case of claim 31 including,
said flap comprising a top flap secured to said first panel.

33. The case of claim 1 including,
said first securing means comprising a hook and loop type securing means.

34. The case of claim 1 including,
said hinge means connecting said first panel side edge and said second panel side edge.

35. The case of claim 1 including,
said first securing means including a first securement part attached to said second panel and a second securement part attached to said first panel and movable to and between a first position for releasable engagement with said first securement part when said first and second panels are in said first position and a second position for releasable engagement with said first securement part when said first and second panels are in said second position.

36. The case of claim 35 including,
said second securement part comprising a panel of material hinged to said first panel and having a hook and loop type of fastening means attached to said panel.

37. A medical supply case for organizing and holding small medical supplies and to be worn or carried by medical personnel comprising:
a first panel having a first panel front side, a first panel rear side, and a first panel side edge,
a second panel connected to said first panel and having a second panel inside side, a second panel outside side, and a second panel side edge,
a hinge means for positioning said first and second panels relative to each other alternatively in a first position wherein said first panel front side is generally adjacent and facing said second panel inside side and in a second position wherein said second panel outside side is generally adjacent and facing said first panel rear side,
a first securing means for releasably securing said first and second panels in said first position,
a supply pocket on said first panel front side,
a supply pocket on said second panel outside side,
said first panel having a side one portion and a side opposite portion,
a first side panel connected to said one portion, and having a first side panel inside side and first side panel outside side,
a second side panel connected to said opposite portion, and having a second side panel inside side and a second side panel outside side,
said first and second side panels being positionable in a one side panel position in which said inside sides of said first and second side panels are generally facing said first panel front side and another side panel position in which said outside sides of said side panels are generally facing said first panel rear side, and
said hinge means comprising a generally vertically-disposed hinge structure when said supply case is worn by the medical personnel.

38. The case of claim 37 including,
said first and second panels being in said first position when said first and second side panels are in said one side panel position.

39. The case of claim 37 including,
said first and second panels being in said first position when said first and second side panels are in said another side panel position.

40. The case of claim 39 including,
said first and second panels being in said second position when said first and second side panels are in said one side panel position.

41. The case of claim 37 including,
a securing means for releasably securing said first and second side panels together in said one side panel position.

42. The case of claim 37 including,
a securing means for releasably securing said first and second side panels together in said another side panel position.

43. The case of claim 37 including,
said first panel having a first panel top edge,
a top flap secured to and along said first panel top edge, and
said top flap being secured to said second side flap when said first and second panels are in said first position.

44. The case of claim 37 including,
said first side flap being generally the same size and shape as said second panel.

45. The case of claim 37 including,
said first side flap folding onto said first panel rear side when said second panel is in said second position.

46. The case of claim 45 including,
said second side flap folding on and being releasably secured to said first side flap, when said first and second panels are in said second position.

47. The case of claim 37 including,
said first side flap and said first panel being formed from a single continuous piece of material.

48. The case of claim 47 including,
said material comprising a plastic.

49. The case of claim 47 including,
said material comprising a fabric.

50. The case of claim 37 including,
said first side flap folding onto said second outside side when said first and second panels are in said first position, and said second side flap then folding onto and being secured to said first side flap.

51. The case of claim 37 including,
said first panel having a first panel top edge which is generally perpendicular to said first panel side edge, and
sid hinge means being disposed generally along said first and second panel side edges and connecting them together.

52. The case of claim 37 including,
an attaching means for attaching said first panel to medical personnel.

* * * * *